US006251611B1

(12) United States Patent
Puschett

(10) Patent No.: US 6,251,611 B1
(45) Date of Patent: Jun. 26, 2001

(54) METHOD OF DETERMINING VOLUME DEPENDENT HYPERTENSION VIA REDUCTION IN PHOSPHORYLATION

(75) Inventor: Jules B. Puschett, New Orleans, LA (US)

(73) Assignee: Tulane University Medical Center, New Orleans, LA (US)

( * ) Notice: Subject to any disclaimer, the term of this patent is extended or adjusted under 35 U.S.C. 154(b) by 0 days.

(21) Appl. No.: 08/938,061

(22) Filed: Sep. 26, 1997

(51) Int. Cl.$^7$ .......................... G01N 33/53; G01N 31/00; G01N 33/48; C12N 11/02

(52) U.S. Cl. .......................... 435/7.1; 435/7.1; 435/7.2; 435/7.21; 435/7.24; 435/7.25; 435/174; 435/177; 435/178; 435/219; 435/355; 435/372; 436/15; 436/16; 436/501; 436/517; 436/63; 424/130.1; 424/141.1; 424/145.1; 424/158.1; 514/52; 514/258; 210/647; 530/387

(58) Field of Search .................................... 435/7.24, 177, 435/7.1, 7.21, 7.2, 7.25, 174, 219, 178, 355, 372; 424/130.1, 145.1, 141.1, 158.1; 514/258, 52; 210/647; 530/387; 436/501, 16, 517, 63, 15

(56) References Cited

U.S. PATENT DOCUMENTS

| | | |
|---|---|---|
| 4,321,120 | 3/1982 | Nardi et al. . |
| 4,665,019 | 5/1987 | Hamlyn et al. . |
| 4,840,894 | 6/1989 | Schachter et al. . |
| 5,844,091 | 12/1998 | Blaustein et al. . |

OTHER PUBLICATIONS

Laemmli; Cleavage of Structural Proteins During the Assembly of the Head of Bacteriophage T4, Nature, 227:pp. 680–685 (1970).

Labrie, et al., Adenohypophyseal Secretory Granules, J. Biol. Chem., 246:pp. 7311–17 (1971).

Weller, et al., Protein Kinase Activity in Membrane Preparations from Ox Brain, J. Biochem, 132:pp. 483–492 (1973).

Ueda et al., Regulation of Endogenous Phosphorylation of Specific Proteins in Synaptic Membrane Fractions from Rat Brain by Adenosine 3':5' Monophosphate, J. Biol. Chem. 248:pp. 8295–8305 (1973).

Chang, et al., Cyclic Adenosine Monophosphate–Dependent Phosphorylation of Specific Fat Cell Membrane Proteins by an Endogenous Membrane–Bound Protein Kinase, J. Biol Chem, 249:pp. 6854–65 (1974).

Pinkett, et al., Phosphorylation of Muscle Plasma Membrane Protein by a Membrane–Bound Protein Kinase, Biochem Biophys Acta, 372:pp. 379–387 (1974).

(List continued on next page.)

*Primary Examiner*—Long V. Le
*Assistant Examiner*—Gailene R. Gabel
(74) *Attorney, Agent, or Firm*—Arnold B. Silverman; Eckert Seamans Cherin & Mellott, LLC

(57) ABSTRACT

A method of determining the presence of chronic volume dependent hypertension is provided wherein a determination is made as to whether there has been a substantial reduction in phosphorylation of the blood-derived protein or renal proximal brush border membrane protein and if such reduction exists concluding that chronic volume dependent hypertension exists in a patient. The method may advantageously be practiced by employing blood serum or blood plasma as the body specimen containing the protein in determining whether a patient has chronic volume dependent hypertension, a cellular component of the blood, such as a blood-derived protein coming from the plasma membrane of lymphocytes. The method may include subsequent therapeutic patient treatment. Related diagnostic apparatus is also provided.

11 Claims, 3 Drawing Sheets

OTHER PUBLICATIONS

Bradford, A Rapid and Sensitive Method for the Quantitation of Microgram Quantities of Protein Utilizing the Principle of Protein–dye Binding. Anal Biochem, 72:pp. 248–254 (1976).

Pamnani et al. Altered Activity of the Sodium–Potassium Pump in Arteries of Rats with Steroid Hypertension, Clin. Sci. Mol. Med., 55:pp. 41s–43s (1978).

Huang, et al. Bilateral Renal Function Responses to Converting Enzyme Inhibitor (SQ 20, 881) in two–kidney, one clip Goldblatt Hypertensive Rats, Hypertension, 3:pp. 285–293 (1981).

Weinman, et al., Protein Kinase C Activates the Renal Apical Membrane $Na^+/H^+$ Exchanger J. Membr. Biol., 93:pp. 133–139 (1986).

Puschett et al. Volume Expansion Induced Changes in Renal Tubular Membrane Protein Phosphorylation, Biochem. Biophys. Res. Commun., 143:pp. 74–80 (1987).

Weinman et al., cAMP–associated Inhibition of $Na^+$–$H^+$ Exchanger in Rabbit Kidney Brush–Border Membranes, Am. J. Physiol., 252:F19–F25 (1987).

Schenk, The Pathogenesis of DOCA–salt Hypertension, J. Pharmacol. Toxicol Methods, 27:pp. 161–170 (1992).

Laminski, et al., Phosphorylation of Endogenous Protein in Primate Kidney. Effects of Cyclic AMP, Comp. Biochem. Physiol. 103B:pp. 267–273 (1992).

Hood, Immunology, Second Edition, Jan. 1, 1984, pp. 52–58.*

Gaia et al., Heat shock protein 72 in cardiac and sleletal muscles during hypertension, Mol Cell Biochem 146(1):1–6, May 10, 1995.*

Motilal B. Pamnani Et Al., Altered activity of the sodium–potassium pump in arteries of rats with steroid hypertension, Clinical Science and Molecular Medicine, (1978), vol. 55, pp. 41s–43s, Bethesda, Maryland, U.S.A.

E.J. Weinman and S. Shenolikar, Protein Kinase C Activates the Renal Apical Membrane Na+/H+ Exchanger, J. Membrane Biol., (1986) vol. 93, pp. 133–139, Houston, Texas, U.S.A.

Tai C. Chen Et Al., Volume Expansion–Induced Changes in Renal Tubular Membrane Protein Phosphorylation, Biochemical and Biophysical Research Communications, (Feb. 27, 1987), vol. 143, No. 1, pp. 74–80, Pittsburgh, PA, U.S.A.

A. Nishi Et Al., Renal Na+, K+–ATPase in Dahl salt–sensitive rats: K+ dependence, effect of cell environment and protein kinases, (1993) Acta Physiol Scand. vol. 149, pp. 377–384, Stockholm, Sweden.

* cited by examiner

METHOD OF DETERMINING VOLUME DEPENDENT HYPERTENSION VIA REDUCTION IN PHOSPHORYLATION

BACKGROUND OF THE INVENTION

1. Field of the Invention

The present invention provides a means for determining whether a patient has volume dependent hypertension and, more specifically, it provides such a method based upon determining if a substantial reduction in phosphorylation of a specific protein exists. The invention also relates to a diagnostic apparatus employable in making such determination.

2. Description of the Prior Art

Elevated blood pressure or hypertension has long been recognized as a health problem. It is a very common disease which can have widespread effects on a patient's body and frequently, unlike numerous other diseases, is asymptomatic.

Despite known means of measuring blood pressure of a patient as by a sphygmomanometer, for example, there is lacking an accurate reliable means of detecting the presence of volume dependent hypertension involving higher arterial blood pressure by use of a body specimen, such as blood serum or blood plasma.

From a pathogenic standpoint, essential hypertension may be divided into two broad categories (a) volume expansion, hypertension, and (b) vasoconstriction hypertension. It has been estimated that about 30 to 40 percent of human essential hypertension may be permanently related to volume expansion hypertension, especially in certain demographic groups. Previous studies participated in by the present inventor have demonstrated an alteration in the phosphorylation of a proximal tubular membrane protein following acute saline expansion of the experimental rat (Puschett et al. Volume Expansion Induced Changes in Renal Tubular Membrane Protein Phosphorylation, Biochem. Biophys. Res. Commun., 143: pp. 74–80 (1987)).

SUMMARY OF THE INVENTION

The present invention has met the above-described need by providing a method of determining the presence of volume dependent hypertension which includes determining if there has been a substantial reduction in phosphorylation of a blood-derived protein present in blood and, if such reduction exists, concluding that volume dependent hypertension exists. It may be employed in determining the presence of chronic volume expansion hypertension in a patient and may effectively be determined independent of the presence or absence of vasoconstriction hypertension in the patient.

It is preferred that the reduction in phosphorylation exceed about 20 percent and preferably be at least about 20 to 30 percent before making a determination that chronic volume dependent hypertension exists. A blood component, such as blood serum or blood plasma containing the blood protein, may be employed in the practice of the method of the present invention. One embodiment employs an antibody to detect the protein.

After a determination of the presence of chronic volume expansion hypertension, one may employ any desired means of treating the patient to effect reduction of the same, while periodically monitoring progress.

The invention also contemplates apparatus for determining the presence of chronic volume dependent hypertension in a patient which includes means for receiving a patient blood specimen containing the blood-derived protein and means for determining if the protein has substantially reduced phosphorylation. The blood specimen may be blood serum or blood plasma. It may also employ an antibody.

It is the object of the present invention to provide a method and associated apparatus for determining the presence of chronic volume expansion hypertension in a patient in a reliable and rapid manner.

It is further an object of the present invention to provide apparatus which facilitates such a determination and may employ a patient body specimen, such as blood serum or blood plasma.

It is yet another object of the present invention to provide such a diagnostic system which will rely on substantial reduction in phosphorylation of a blood-derived protein in effecting a determination that chronic volume expansion hypertension exists.

It is a further object of the present invention to provide such a system which is reliable and will effectively distinguish chronic volume expansion hypertension from acute volume expansion hypertension, vasoconstriction hypertension and other types of hypertension.

It is another object of the present invention to provide such a method and related apparatus which is economical and may be practiced by paraprofessional personnel in an accurate manner.

These and other objects of the invention will be more fully understood from the following description of the invention on reference to the illustrations appended hereto.

DESCRIPTION OF THE PREFERRED EMBODIMENTS

Figure 1:
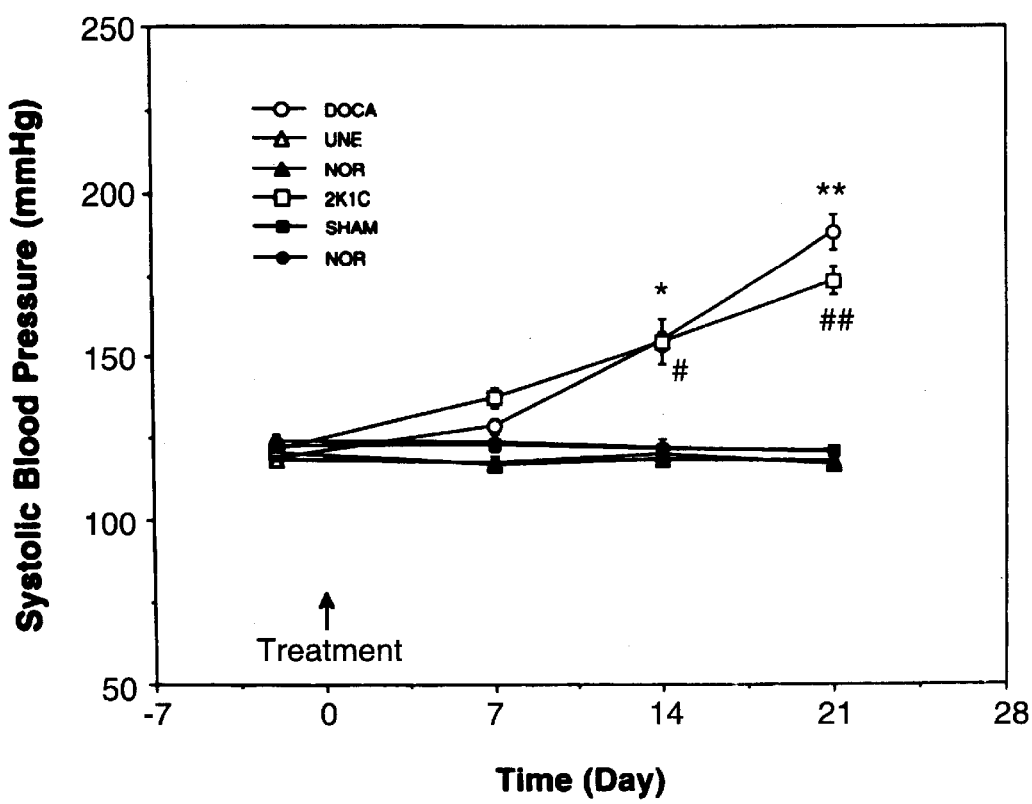
FIG. 1 is a plot of changes in systolic blood pressure versus time reflecting the results of animal studies.

The term "blood-derived protein" as employed herein refers to a protein present in a human's blood plasma or blood serum which is identical or similar to a human renal brush border membrane protein and has Mr=72,000 Daltons.

As used herein, the term "patient" refers to human beings.

The term "body specimen" means a specimen obtained from a patient which contains a protein of interest and expressly includes blood serum and blood plasma.

The preferred practice of the present invention for determining the presence of chronic volume dependent hypertension includes determining if there has been a substantial reduction in phosphorylation of the blood-derived protein which is identical or similar to the renal proximal brush border membrane protein. In one approach, the blood-derived protein may come from a cellular element in the blood such as the plasma membrane of lymphocytes. The base line for such evaluations may be obtained through evaluation of normal human patients. If such reduction or down-regulation exists, it is concluded that chronic volume dependent hypertension exists. The method provides a method capable of making this determination independently of whether vasoconstriction hypertension or other types of hypertension exists in the patient. The blood-derived protein has an Mr=72,000.

In general it is preferred that there be at least about a 20 percent reduction in phosphorylation below the lower limit of the range of normal human patients before the reduction is deemed to indicate the presence of chronic renal volume expansion hypertension and preferably a reduction in the range of at least about 20 to 30 percent reduction. This reduction is determined by determining the phosphorylation of the patient's blood-derived protein and comparing it with an established normal range.

The body specimen employed in practicing the method of the present invention may advantageously be a blood-derived specimen, such as blood serum or blood plasma. In one embodiment, an assay employing specific antibody bonding could be employed to detect the renal proximal brush border membrane protein in the blood specimen. In another embodiment which employs a chemical approach, purification and identification of the 72,000 Mr protein may be effected such as by, for example, initial gel separation followed by identification of the amino acid sequence of the protein.

In the event that it is determined that a patient has volume-dependent hypertension after completion of the diagnostic evaluation, the patient may be treated in a therapeutically beneficial manner, such as efforts to control the same by medication such as the use of diuretics, for example. Also employable would be dietary guidance with the objective of weight reduction and controlling consumption of sodium and other potentially detrimental materials and combinations thereof. Exercise programs may also be employed. It will be appreciated that the present invention focuses on the detection of the presence of chronic volume dependent hypertension with subsequent treatment of the patient along any desired lines being effected once the presence of volume dependent hypertension has been confirmed.

The apparatus of the present invention may include means for receiving a patient's body blood serum or blood plasma specimen which may be one or more suitably sized and shaped containers or multiple recesses in a tray or the like containing the specific blood-derived protein and means for determining if the protein has substantially reduced phosphorylation. The means for making this determination may include an assay using antibody methodology.

The apparatus, which may be a kit, preferably has means for determining either the level of phosphorylation or the reduction if phosphorylation reduction exceeds 20 percent or falls within the range of at least about 20–30 percent. If the reduction exceeds these numerical standards, this indicates that volume expansion hypertension exists in the patient. If desired, automated equipment may be employed to effect or assist with the determination.

EXAMPLE

In order to confirm the reliability of substantial reduction in phosphorylation of the blood-derived protein (Mr=72,000), experiments were performed on rats selecting two models of experimental hypertension which exemplify the two major modes of chronic essential hypertension (high blood pressure).

In the first model, the effects of chronic volume expansion employing DOCA-salt hypertension as discussed in Schenk, The Pathogenesis of DOCA-salt Hypertension, J. Pharmacol. Toxicol Methods, 27: pp. 161–170 (1992) was involved. The second model related to chronic vasoconstriction. The two-kidney, one clip (2K1C) model was prepared in accordance with the procedure of Huang, et al. Bilateral Renal Function Responses to Converting Enzyme Inhibitor (SQ 20, 881) in two-kidney, one clip Goldblatt Hypertensive Rats, Hypertension, 3: pp. 285–293 (1981). The experiments in connection with both types of hypertension were conducted with a view toward determining the effect of these types of hypertension on phosphorylation. Phosphorylation and dephosphorylation of membrane proteins are mediated by membrane-bound and cytosolic protein kinases, phosphoprotein and phosphatases. In some membranes the phosphorylation of intrinsic proteins by the particular protein kinase is simulated by cyclic AMP (cAMP). See, for example, Ueda et al., Regulation of Endogenous Phosphorylation of Specific Proteins in Synaptic Membrane Fractions from Rat Brain by Adenosine 3':5' Monophosphate, J. Biol. Chem. 248: pp. 8295–8305 (1973); Weller, et al., Protein Kinase Activity in Membrane Preparations from Ox Brain, J. Biochem, 132: pp. 483–92 (1973); and Chang, et al., Cyclic Adenosine Monophosphate-Dependent Phosphorylation of Specific Fat Cell Membrane Proteins by an Endogenous Membrane-Bound Protein Kinase, J. Biol Chem, 249: pp. 6854–65 (1974). In other systems, however, cyclic nucleotides have little or no effect. See Labrie, et al., Adenohypophyseal Secretory Granules, J. Biol. Chem., 246: pp. 7311–17 (1971), and Pinkett, et al., Phosphorylation of Muscle Plasma Membrane Protein by a Membrane-Bound Protein Kinase, Biochem Biophys Acta, 372: pp. 379–87 (1974). As a result, no unifying pattern of the regulation of membrane protein phosphorylation by cyclic nucleotides or other second messengers has resulted. The responses and relationships between the state of membrane protein phosphorylation and the functions of the cells appears to be variable and tissue specific. For example, the $Na^+$-$H^+$ antiporter of renal brush border membranes is inhibited by cAMP and stimulated by protein kinase C. See Weinman et al., cAMP-associated Inhibition of $Na^+$-$H^+$ Exchanger in Rabbit Kidney Brush-Border Membranes, Am. J. Physiol., 252: F19-F25 (1987); and Weinman, et al., Protein Kinase C Activates the Renal Apical Membrane $Na^+$/$H^+$ Exchanger. J. Membr. Biol., 93: pp. 133–39 (1986).

The following animal preparatory procedures were employed with the DOCA-salt hypertensive rats:

Male Sprague-Dawley rats, weighing 125–150 g (Charles River, Wilmington, Mass.), were randomly divided into three groups: (1) DOCA-salt group-rats underwent unilateral nephrectomy and were given an initial injection of 12.5 mg of deoxycorticosterone acetate (DOCA) followed by 6.5 mg weekly which was coupled with 1 percent saline as drinking water (Pamnani et al. Altered Activity of the Sodium-Potassium Pump in Arteries of Rats with Steroid Hypertension, Clin. Sci. Mol. Med., 55: pp. 41s–43s (1978); (2) Uninephrectomized control group (UNE)-rats underwent unilateral nephrectomy and were given tap water ad libitum, (3) Normal group-normal rats drank tap water ad libitum and were not subject to surgery. All three groups were maintained on normal rat chow. Systolic blood pressure was measured weekly by the tail-cuff method.

The two-kidney, one clip Goldblatt hypertensive rats (2K1C) were prepared as follows: Male Sprague-Dawley rats (Charles River, Wilmington, Mass.), weighing 125–150 g, were randomly divided into three groups: (1) 2K1C group-rats were anaesthetized with pentobarbital sodium (50 mg/kg, i.p.). The left renal artery of each animal was isolated through a flank incision; and a silver clip (0.25 mm i.d.) was placed on the renal artery (4); (2) Sham-operated group (Sham)-the operative procedure was the same as in the 2K1C group with the exception that no clip was placed on the renal artery; (3) Normal group-rats did not undergo any operative procedure. All rats were fed normal chow and tap water ad libitum. Systolic blood pressure was measured weekly. In this manner, three groups of the DOCA-salt group rats and three groups of the (2K1C) rats were created.

The preparation of the rat renal proximal brush border membrane vesicles was accomplished in the following manner: When the systolic blood pressure in the DOCA and the 2K1C rat groups became elevated compared with each of the control groups (usually in 3–4 weeks), the kidney cortex was removed to prepare the proximal brush border membrane vesicles by a calcium precipitation method as described in Kempson et al., Inhibition of Renal Brush Border Phosphate Transport and Stimulation of Renal Gluconeogenesis by Cyclic AMP and Parathyroid Hormone, Biochem., Pharmacol., 32: pp. 1533–37 (1983). Vesicles were utilized only if there was at least an 8-fold enrichment in gamma-glutamyl transpeptidase activity in the proximal brush border membrane fraction compared to the original cortical homogenate. Phosphorylation of the proximal brush border member protein by an intrinsic protein kinase was carried out by a modification of the methods of Hammerman, et al., Cyclic AMP. Independent Protein Phosphorylation in Canine Renal Brush Border Membrane Vesicles is Associated with Decreased Phosphate Transport. J. Biol. Chem. 257: pp 992–99 (1982). The final incubation mixture (in 200 $\mu$l) contained 500 $\mu$g protein, 5 mM MES/Tris-HCl (pH 6.5), 10 mM KF, 10 $\mu$M ATP containing approximately 2.5 $\mu$Ci of [$\gamma$-$^{32}$P]-ATP. Studies were performed in the presence and absence of 10 $\mu$M cyclic AMP. The mixture was preincubated in a 30° C. water bath for one minute in the absence of ATP. Incubation was continued for another minute after the addition of the nucleotide. The phosphorylation reaction was then terminated by the addition of 200 $\mu$l of an ice-cold 125 mM Tris-HCl buffer (pH 6.8) containing 4 percent SDS (w/v) followed by boiling for 3 minutes in preparation for electrophoresis.

The test results reported herein were determined by SDS polyacrylamide gel electrophoresis, autoradiography and densitometry. Samples containing up to 65 $\mu$g of renal brush border membrane protein were loaded on SDS-polyacrylamide slab gels, and electrophoresis was performed according to the method of Laemmli; Cleavage of Structural Proteins During the Assembly of the Head of Bacteriophage T4, Nature, 227: pp. 680–685 (1970). The final concentrations in the resolving gel were as follows: 7.5 percent acrylamide, 0.375 M Tris-HCl (pH 8.8), 0.1 percent SDS, 0.05 percent (by volume) tetramethylenediamine (TEMED) and 0.075 percent ammonium persulfate. The running buffer contained 0.025 M Tris-HCl (pH 8.6), 0.192 M glycine and 0.1 percent SDS. SDS-polyacrylamide gels were calibrated for molecular weights using known standard protein: ovalbumin (Mr=45,000), bovine serum albumin (Mr=66,200), phosphorylase B (Mr=97,400), $\tau$=galactosidase (Mr=116,250) and myosin (Mr=200,000). Protein concentration was determined by the method of Bradford using bovine serum albumin as a standard. See Bradford, A Rapid and Sensitive Method for the Quantitation of Microgram Quantities of Protein Utilizing the Principle of Protein-dye Binding. Anal Biochem, 72: pp. 248–54 (1976).

Autoradiography and densitometry were performed in accordance with Laminski, et al., Phosphorylation of Endogenous Protein in Primate Kidney. Effects of Cyclic AMP, Comp. Biochem. Physiol. 103B:pp 267–73 (1992). Coomassie blue-stained and dried gels were exposed to Kodak X-ray films (X-Omat, AR) at 70° C. Scan traces were recorded with an Ultroscan XL laser densitometer (Pharmacia, LKB) and analyzed by using the computer GelScan XL Software (Version 2.1, Pharmacia).

Data is expressed as mean±SEM, with statistical significance being calculated by Student's test and the ANOVA test.

Referring to FIG. 1, there is shown a plot of systolic blood pressure in mm Hg versus time in days. The study involved ten rats in each of the three DOCA categories: (a) DOCA-salt; (b) UNE-uninephrectomized; and (c) NOR, normal group. The 2K1C study involved eight rats in each of the three groups: (a) 2K1C; (b) SHAM, sham-operated group; and (c) NOR, normal group.

As shown in FIG. 1, the DOCA-salt rats showed a gradual rise in systolic blood pressure from a mean value of 119.0±1.5 mm Hg to 128.9±2.1 mm Hg by the 7th day of treatment and to 188.2±5.3 mm Hg ($p<0.001$) by the 21st day. The systolic blood pressure in the 2K1C rats increased from 121.4±1.7 mm Hg to 137.6±3.0 mm Hg by the first week after surgery and to 173.5±4.4 mm Hg by the 21st day ($p<0.001$). No significant change in systolic blood pressure occurred in the UNE or the Normal rats for the DOCA group (117.0±1.3 mm Hg and 118.2±1.5 mm Hg, respectively, $p<0.05$) or in the Sham or Normal rats for the 2K1C group (121.1±1.7 mm Hg and 120.8±1.9 mm Hg, respectively, $p>0.05$) at day 21.

This data verifies the fact that only the two groups of rats which were either treated with DOCA or in which a clip was applied to the renal artery developed hypertension, whereas the other groups did not.

Figure 2:
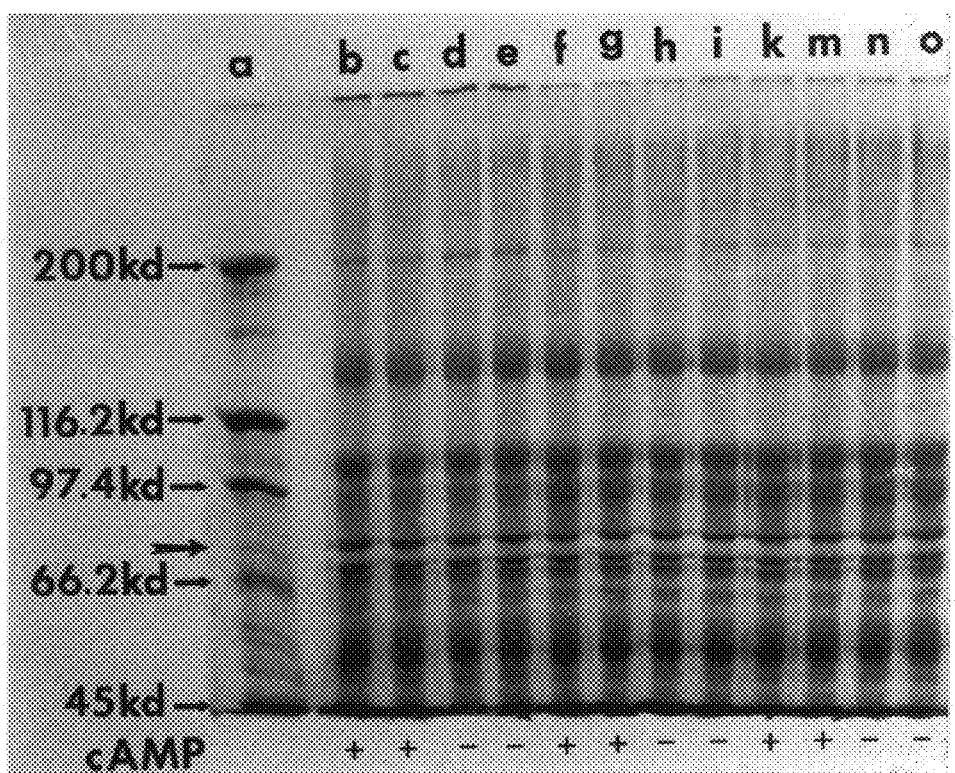
FIG. 2 is an SDS-polyacrylamide gel electrophoresis (PAGE) profile prepared from phosphorylated brush border membrane proteins.
Figure 3:
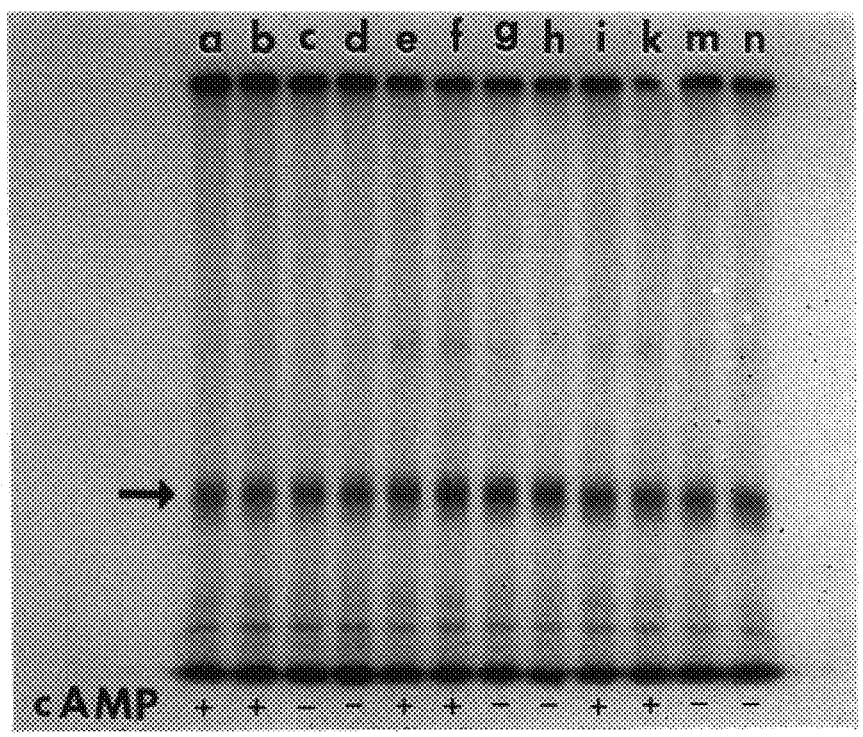
FIG. 3 is an autoradiogram of phosphorylated brush border membrane protein.

The phosphorylation of renal brush border membrane protein from DOCA, UNE and Normal group rats is illustrated in SDS-polyacrylamide gel electrophoresis (PAGE) profiles presented in FIG. 2 and in the autoradiogram provided in FIG. 3. SDS-polyacrylamide gel electrophoresis (PAGE) profile of phosphorylated brush border membrane proteins prepared from DOCA-salt (DOCA, lanes b–e), uninephrectomized (UNE, lanes f–i) and normal (NOR, lanes k–o) rats are shown. Protein bands were stained by Coomassie blue. Lane a is a profile of five standard proteins with molecular weights as indicated. Lanes b–o represent a typical electrophoresis profile of brush border membrane proteins that were $^{32}$P-phosphorylated in the presence and absence of cyclic AMP. The arrow points to the 72,000 Mr brush border membrane protein. In FIGS. 2 and 3, the "+" and "−" signs indicate whether or not cAMP was added.

The addition of cyclic AMP did not affect the phosphorylation of the Mr=72,000 protein. The phosphorylation of this protein from DOCA group rats showed a significant attenuation ($p<0.01$) compared with those from UNE and normal rats (Table 1). Table 1 shows the effects of DOCA-salt treatment and renal vasoconstriction on the phosphorylation of a 72,000 Mr brush border membrane protein from DOCA-salt hypertensive (DOCA), uninephrectomized (UNE) and control (NOR) rats compared to those obtained in two-kidney, one clip (2K1C), sham-operated (SHAM) and control rats (NOR).

TABLE 1

|   | NOR<br>n = 10 | UNE<br>(n = 10) | DOCA<br>(n = 20) | NOR<br>(n = 8) | SHAM<br>(n = 8) | 2K1C<br>(n = 8) |
|---|---|---|---|---|---|---|
| +cAMP | 1.973 ± 0.48 | 1.722 ± 0.43 | 1.218 ± 0.33 | 2.407 ± 0.30 | 2.704 ± 0.51 | 2.315 ± 0.39 |
| −cAMP | 2.051 ± 0.52 | 1.788 ± 0.44 | 1.389 ± 0.37 | 2.447 ± 0.29 | 2.679 ± 0.51 | 2.504 ± 0.45 |
| P |   | NS+ vs NOR | <0.01 vs NOR & vs UNE |   | NS vs NOR | NS vs NOR & SHAM |

°The data express the mean ± SEM of relative area units under the peak in the densitometry tracings of autoradiogram of the $M_r$ = 72,000 brush border membrane protein.

╪ +cAMP and −cAMP indicate, respectively, the presence and absence of cyclic AMP in the incubation mixture.

+NS = Not statistically significant.

FIG. 3 shows an autoradiogram of phosphorylated brush border membrane proteins from DOCA-salt (DOCA, lanes a–d), uninephrectomized (UNE, lanes e–h) and normal (NOR, lanes i–n) rat groups. The arrow shows the brush border membrane protein ($M_r$=72,000) which is phosphorylated and cAMP-independent.

Figure 4:
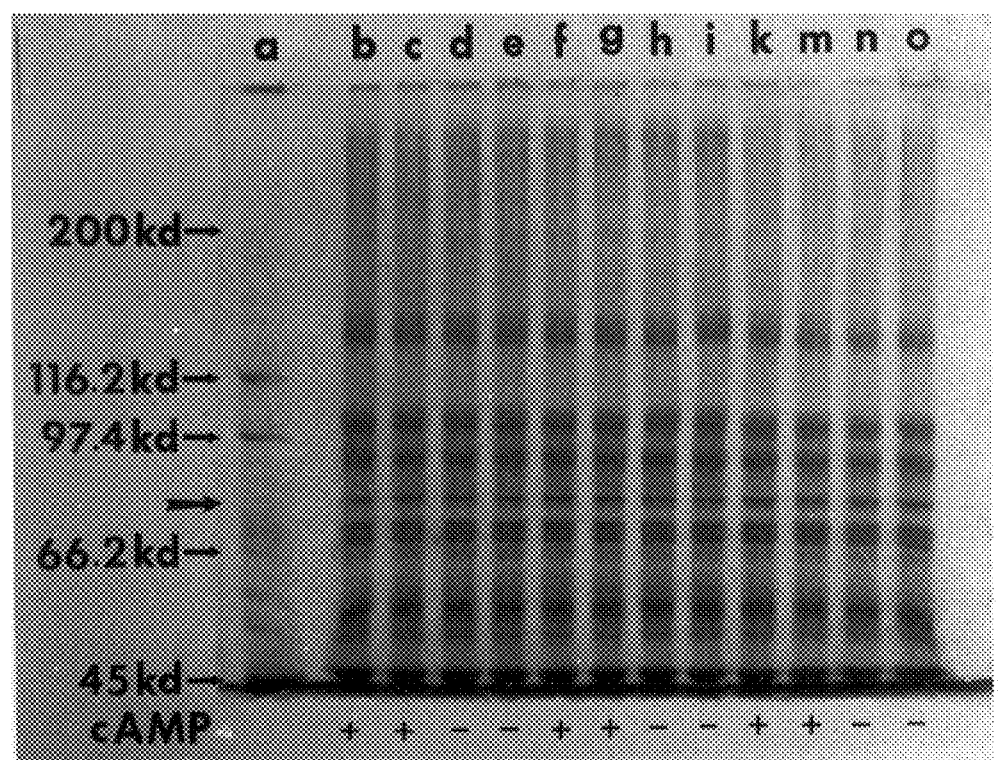
FIG. 4 is an SDS-polyacrylamide gel electrophoresis (PAGE) profile of phosphorylated brush border membrane proteins prepared from different experiments than those employed in FIG. 2.
Figure 5:
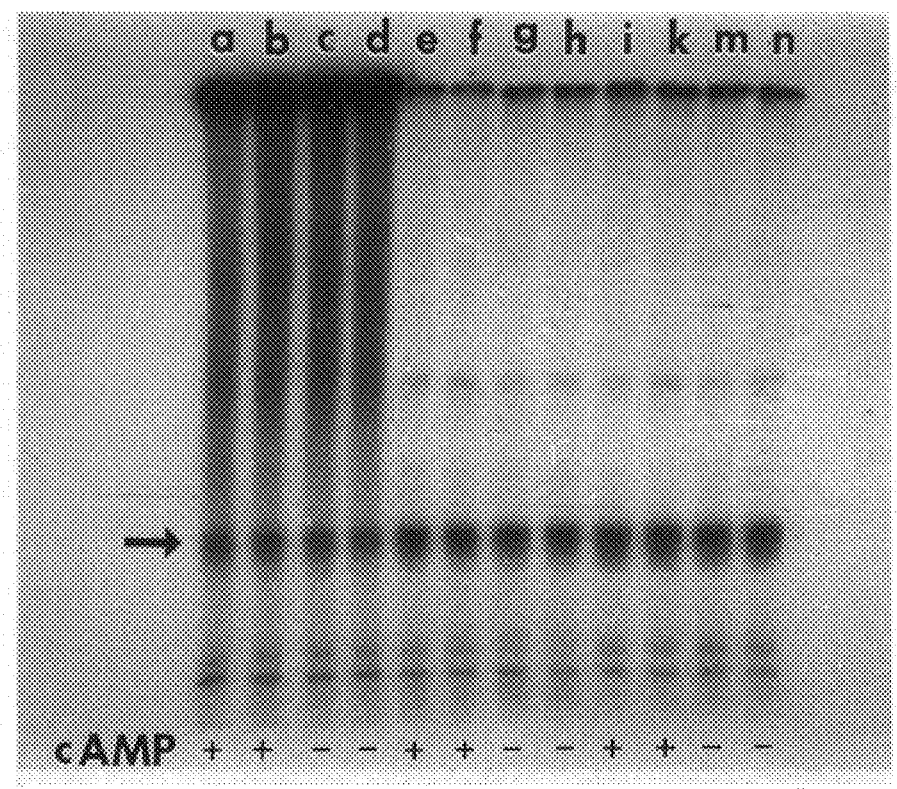
FIG. 5 is an autoradiogram of phosphorylated brush border membrane proteins of the kidneys shown in FIG. 4.

Phosphorylation of the brush border membrane proteins on SDS-PAGE and on autoradiography from 2K1C, Sham and Normal rats is presented in FIGS. 4 and 5, respectively. FIG. 4 shows an SDS-polyacrylamide gel electrophoresis (PAGE) profile of phosphorylated brush border membrane proteins prepared from two-kidney, one clip (2K1C, lanes b–e), sham-operated (SHAM, lanes f–i) and control (NOR, lanes k–o) rats. Protein bands were stained with Coomassie blue.

FIG. 5 shows an autoradiogram of phosphorylated brush border membrane proteins from two-kidney, one clip (2K1C, lanes a–d), sham-operated (SHAM, lanes e–h) and control (NOR, lanes i–n) rats. The arrow shows the brush border membrane protein ($M_r$=72,000) which is phosphorylated and is cAMP-independent.

As opposed to the protein seen in the DOCA-salt animals, the phosphorylation of the $M_r$=72,000 brush border membrane protein in the 2K1C animals showed no difference from those in either the Sham or Normal rats, respectively ($p<0.05$, Table 1). The phosphorylation of this protein was not influenced by cAMP.

It will be appreciated that the foregoing tests involved the volume expansion hypertension model created through the administration of DOCA which was compared with those obtained utilizing a model of primary vasoconstriction hypertension which lacks the expansion component, i.e., 2K1C. The results show that down-regulation of the phosphorylation of this renal brush border protein occurred in chronically expanded rats, but there was no change in the 2K1C Goldblatt hypertensive animals. This is to be contrasted with the inventor's prior findings regarding acute volume expansion as reported in Puschett et al., Volume Expansion-Induced Changes in Renal Tubular Membrane Protein Phosphorylation, Biochem. Biophys. Res. Commun., 143:pp.74–80 (1987). The tests also clearly showed that the phosphorylation of the brush border membrane protein was not influenced by cAMP. It will be appreciated that the down-regulation of the phosphorylation of renal proximal brush border membrane protein not only may serve as a diagnostic marker for disorders characterized by volume expansion hypertension, but also may have a role in the pathogenesis of this type of hypertension.

The alteration of the phosphorylation of the renal brush border membrane protein produced by chronic extracellular fluid volume expansion may result in an alteration in membrane ionic transport. This phenomenon may have relevancy to the pathogenesis of this type of hypertension, as well as serving as a marker to identify this type of hypertension.

It will be appreciated that the present invention provides methods and related apparatus for employing a patient's blood and determining whether chronic volume expansion hypertension exists in the patient, thereby permitting appropriate therapeutic measures to be taken. The system is particularly important in view of the serious health consequences of chronic volume expansion hypertension coupled with the fact that patients are frequently asymptomatic for a period of time. The present invention may also be employed to identify patients who are at risk for development of volume expansion mediated hypertension by studying first degree relatives of patients who are identified as positive in the test of the present invention. All of this is accomplished by determining that there has been substantial reduction in phosphorylation of the blood-derived protein in the patient. In the preferred embodiment, the substantial reduction in phosphorylation will be at least 20 percent and most preferably at least about 20 to 30 percent before a determination that volume dependent hypertension exists will be made.

It will be appreciated that the experiential data contained herein confirms that down-regulated phosphorylation of a renal brush border membrane protein permits diagnostic determination of the presence or absence of chronic volume expansion hypertension. The related blood-derived protein obtained from human blood plasma or blood serum may be employed in making such a determination.

The invention also contemplates a method for making such determination and providing therapeutic treatment to a patient as by administering appropriate medication with the dosage corresponding to the severity of the volume dependent hypertension and the health of the patient in any other respects. Appropriate diet and exercise may also be recommended.

The invention also provides apparatus which may be in kit form for determining the presence of volume dependent hypertension in a patient which includes apparatus for receiving a patient specimen containing a blood-derived protein and apparatus for determining if the protein has substantially reduced phosphorylation. Before a determination is made that chronic volume dependent hypertension exists, it is preferred that the substantially reduced phosphorylation be at least 20 percent and most preferably at least about 20 to 30 percent.

The method and apparatus of the present invention is not only employable to make an initial determination of whether a patient has chronic volume dependent hypertension, but also for subsequent monitoring of the effectiveness of therapy employed to treat this condition.

Whereas particular embodiments of the invention have been described herein for purposes of illustration, it will be evident to those skilled in the art that numerous variations of the details may be made without departing from the invention as defined in the appended claims.

I claim:

1. A method of determining the presence of chronic volume dependent hypertension in a human patient comprising:

obtaining from said human patient a blood specimen containing a blood-derived protein with $Mr=72,000$ Dalton which is substantially identical to the human renal brush border membrane protein with $Mr=72,000$ Dalton, wherein said blood-derived protein is obtained from a cellular element of said blood specimen, detecting the blood-derived protein, determining the level of phosphorylation of said blood-derived protein, and correlating the level of phosphorylation relative to the range in normal patients, wherein a substantial reduction in phosphorylation of said blood-derived protein from the normal range is indicative of chronic volume dependent hypertension.

2. The method of claim 1 wherein said blood-derived protein is obtained from the human patient body specimen selected from the group consisting of blood serum and blood plasma.

3. The method of claim 2 wherein said method is employed to determine the presence of chronic volume expansion hypertension in the human patient.

4. The method of claim 2 wherein the substantial reduction in phosphorylation relative to normal patient range is indicative of chronic volume dependent hypertension regardless of the presence or absence of vasoconstriction.

5. The method of claim 2 wherein the substantial reduction in phosphorylation relative to normal patient range is indicative of chronic volume dependent hypertension regardless of the presence or absence of cyclic AMP.

6. The method of claim 2 wherein the substantial reduction in phosphorylation relative to normal patient range is indicative of chronic volume dependent hypertension regardless of the presence or absence of other types of hypertension in said patient.

7. The method of claim 1 wherein said substantial reduction in phosphorylation is determined to exist when said reduction in phosphorylation is a reduction of at least about 20 percent from the range in normal patients.

8. The method of claim 1 wherein the blood serum from the human patient is employed as a source of said blood-derived protein for determining the level of phosphorylation relative to the range in normal patients.

9. The method of claim 8 wherein an antibody specific for said blood-derived protein is employed to detect said blood-derived protein in said patient blood serum.

10. The method of claim 1 wherein said substantial reduction in phosphorylation is determined to exist when said reduction in phosphorylation is a reduction of about 20 to 30 percent from the range of normal patients.

11. The method of claim 1 wherein the blood plasma from the human patient is employed as a source of said blood-derived protein.

* * * * *